(12) United States Patent
Lee et al.

(10) Patent No.: US 9,795,562 B2
(45) Date of Patent: Oct. 24, 2017

(54) METHOD FOR STABILIZING AMPHIPHILIC BLOCK COPOLYMER MICELLE COMPOSITION CONTAINING POORLY WATER-SOLUBLE DRUG

(71) Applicant: SAMYANG BIOPHARMACEUTICALS CORPORATION, Seoul (KR)

(72) Inventors: Sa-Won Lee, Daejeon (KR); Min-Hyo Seo, Daejeon (KR)

(73) Assignee: SAMYANG BIOPHARMACEUTICALS CORPORATION (KR)

( * ) Notice: Subject to any disclaimer, the term of this patent is extended or adjusted under 35 U.S.C. 154(b) by 0 days.

(21) Appl. No.: 14/717,641

(22) Filed: May 20, 2015

(65) Prior Publication Data
US 2015/0250721 A1 Sep. 10, 2015

Related U.S. Application Data

(63) Continuation of application No. 13/960,177, filed on Aug. 6, 2013, which is a continuation-in-part of application No. 12/810,473, filed as application No. PCT/KR2008/006021 on Oct. 13, 2008, now abandoned.

(30) Foreign Application Priority Data

Dec. 31, 2007 (KR) .................. 10-2007-0141181
Oct. 8, 2008 (KR) .................. 10-2008-0098521

(51) Int. Cl.
| *A61K 9/107* | (2006.01) |
| *A61K 31/337* | (2006.01) |
| *A61K 31/436* | (2006.01) |
| *A61K 9/00* | (2006.01) |
| *A61K 9/19* | (2006.01) |
| *A61K 47/34* | (2017.01) |

(52) U.S. Cl.
CPC .......... *A61K 9/1075* (2013.01); *A61K 9/0019* (2013.01); *A61K 9/19* (2013.01); *A61K 31/337* (2013.01); *A61K 31/436* (2013.01); *A61K 47/34* (2013.01)

(58) Field of Classification Search
CPC .......... A61K 9/10; A61K 9/14; A61K 31/337; A61K 9/1075; A61K 47/34; A61K 9/107
See application file for complete search history.

(56) References Cited

U.S. PATENT DOCUMENTS

| 6,045,821 A | 4/2000 | Garrity et al. |
| 6,322,805 B1 | 11/2001 | Kim et al. |
| 6,365,191 B1 | 4/2002 | Burman et al. |
| 6,610,317 B2 | 8/2003 | Straub et al. |
| 6,616,941 B1* | 9/2003 | Seo ............ A61K 9/1075 424/427 |
| 6,803,046 B2 | 10/2004 | Metcalfe et al. |
| 7,229,603 B2 | 6/2007 | Kuperus et al. |
| 2003/0113900 A1 | 6/2003 | Tunnacliffe et al. |
| 2003/0175313 A1 | 9/2003 | Garrec et al. |
| 2003/0180363 A1* | 9/2003 | Seo ............ A61K 9/19 424/486 |
| 2004/0253315 A1* | 12/2004 | Ogawa ............ A61K 9/1075 424/490 |
| 2005/0049359 A1 | 3/2005 | Kelpert et al. |
| 2005/0158271 A1 | 7/2005 | Lee et al. |
| 2006/0057219 A1 | 3/2006 | Nagasaki et al. |
| 2007/0082838 A1 | 4/2007 | De et al. |
| 2007/0135519 A1 | 6/2007 | Hausheer |
| 2007/0225243 A1 | 9/2007 | Horton et al. |
| 2008/0095847 A1 | 4/2008 | Glauser |
| 2008/0166380 A1* | 7/2008 | Yamamoto ............ A61K 9/107 424/400 |
| 2008/0234430 A1 | 9/2008 | Zhao |
| 2009/0012208 A1 | 1/2009 | Madsen et al. |
| 2009/0130085 A1 | 5/2009 | Petersen et al. |
| 2009/0220604 A1 | 9/2009 | Gravett |
| 2009/0304598 A1 | 12/2009 | Gray |

FOREIGN PATENT DOCUMENTS

| CN | 1780865 A | 5/2006 |
| EP | 1670838 B1 | 12/2015 |
| JP | 2003-26566 A | 1/2003 |
| JP | 2003-26812 A | 1/2003 |
| JP | 2003-507514 A | 2/2003 |
| JP | 2004-514734 A | 5/2004 |
| JP | 2004-529934 A | 9/2004 |
| JP | 2005-505674 A | 2/2005 |
| JP | 2007-513970 A | 5/2007 |
| KR | 10-2002-0011992 A | 2/2002 |
| KR | 10-2006-0011337 A | 2/2006 |
| WO | WO 00/71163 A1 | 11/2000 |
| WO | WO 02/087563 A2 | 11/2002 |
| WO | WO 2005/035606 | 4/2005 |
| WO | WO 2005/058279 | 6/2005 |

OTHER PUBLICATIONS

Office Action for Korean application 10-2008-98521 issued Aug. 19, 2010.
Non-Final Office Action for U.S. Appl. No. 12/810,473 mailed Sep. 13, 2012.
Final Office Action for U.S. Appl. No. 12/810,473 mailed Feb. 8, 2013.
Office Action from Chinese Patent Application No. 201410376919.0 (mailed Jan. 14, 2016).

\* cited by examiner

*Primary Examiner* — Tracy Liu
(74) *Attorney, Agent, or Firm* — Merchant & Gould P.C.

(57) ABSTRACT

A method for stabilizing a poorly water-soluble drug-containing amphiphilic block copolymer micelle composition via simplified steps in short time is described. Also described is a stabilized poorly water-soluble drug-containing amphiphilic block copolymer micelle composition having improved stability.

2 Claims, 2 Drawing Sheets

METHOD FOR STABILIZING AMPHIPHILIC BLOCK COPOLYMER MICELLE COMPOSITION CONTAINING POORLY WATER-SOLUBLE DRUG

This application is a continuation of U.S. patent application Ser. No. 13/960,177, filed Aug. 6, 2013, which is a Continuation-in-Part of U.S. patent application Ser. No. 12/810,473, filed 24 Jun. 2010, which is a National Stage Application of International Patent Application No. PCT/KR2008/006021, filed Oct. 13, 2008, which claims the benefit of priority to Korean Patent Application No. 10-2008-0098521, filed Oct, 8, 2008 and Korean Patent Application No. 10-2007-0141181, filed Dec. 31, 2007, the disclosures of all of which are hereby incorporated by reference in their entireties. The International Application was published in English on 9 Jul. 2009 as WO 2009/084801. To the extent appropriate, a claim of priority is made to each of the above disclosed applications.

TECHNICAL FIELD

Example embodiments of the present invention relate to a method for stabilizing an amphiphilic block copolymer micelle composition containing poorly water-soluble drug.

BACKGROUND

Submicronic particulate drug delivery systems using biodegradable polymers have been studied for the purpose of carrying out intravenous administration of drugs. Recently, it has been reported that nanoparticle systems and polymeric micelle systems using biodegradable polymers are useful technological systems that can modify the in vivo distribution of a drug to reduce undesired side effects and can provide improved efficiency. Additionally, because such systems enable targeted drug delivery, they can achieve controlled drug release to target organs, tissues or cells. In fact, such systems are known to have excellent compatibility with body fluids and to improve the solubilization ability of a hardly soluble drug and the bioavailability of a drug.

Recently, there has been reported a method for preparing block copolymer micelles by chemically bonding a drug to a block copolymer comprising a hydrophilic segment and a hydrophobic segment. The block copolymer is an A-B type diblock copolymer polymerized from a hydrophilic segment (A) and a hydrophobic segment (B). In the above-mentioned block copolymer, polyethylene oxide is used as the hydrophilic segment (A) and a polyaminoacid or hydrophobic group-bonded polyaminoacid is used as the hydrophobic segment (B). Such drugs as Adriamycin or indomethacin can be physically encapsulated within the cores of the polymeric micelles formed from the block copolymer, so that the block copolymer micelles can be used as drug delivery systems. However, the polymeric micelles formed from the block copolymer cause many problems in the case of in vivo applications, since they cannot be hydrolyzed in vivo but are degraded only by enzymes, have poor biocompatibility, and cause immune responses, or the like.

Therefore, many attempts have been made to develop core-shell type drug delivery systems having improved biodegradability and biocompatibility.

For example, diblock or multiblock copolymers comprising polyalkylene glycol as a hydrophilic polymer and polylactic acid as a hydrophobic polymer are known to those skilled in the art. More particularly, acrylic acid derivatives are bonded to the end groups of such diblock or multiblock copolymers to form copolymers. The resultant copolymers are subjected to crosslinking to stabilize the polymeric micelles. However, methods for preparing such diblock or multiblock copolymers have difficulties in introducing crosslinkers to the hydrophobic segments of A-B or A-B-A type diblock or triblock copolymers for the polymers to form stable structures via crosslinking. Additionally, the crosslinkers used in the above methods may not ensure safety in the human body because the crosslinkers have not been applied in the human body as yet. Furthermore, the cross-linked polymers cannot be degraded in vivo, and thus cannot be applied for in vivo use.

As another example, a so-called solvent evaporation process has been known as a method for preparing a polymer micelle composition. The solvent evaporation process can be applied as a large-scale process by which poorly water-soluble drugs, which are hardly soluble in water, can be encapsulated within amphiphilic block copolymer micelles. However, utilization of the solvent evaporation process is limited with respect to the selection of a solvent, because the solvent should be an organic solvent in which both poorly water-soluble drug and the polymer can be dissolved, and should have such a low boiling point that it can be volatilized via evaporation. In addition, the organic solvent should be a pharmaceutically acceptable solvent, whose residue does not adversely affect the human body. Further, the solvent evaporation process essentially includes a step of exposing reagents to high temperature for a long period of time, and thus it may cause such problems as degradation of pharmaceutically active ingredients or decreased pharmacological effects.

SUMMARY OF THE INVENTION

Technical Problem

Therefore, in an effort to solve the above-described problems associated with the related art, there is provided a method for stabilizing a poorly water-soluble drug-containing amphiphilic block copolymer micelle composition via simplified steps in short time.

There is also provided a stabilized poorly water-soluble drug-containing amphiphilic block copolymer micelle composition having improved stability.

Technical Solution

In an aspect, there is provided a method for stabilizing a poorly water-soluble drug-containing amphiphilic block copolymer micelle composition, comprising: (a) dissolving poorly water-soluble drug and an amphiphilic block copolymer into an organic solvent; and (b) adding an aqueous solution containing an ionizable salt thereto to form polymeric micelles.

In another aspect, there is provided a stabilized poorly water-soluble drug-containing amphiphilic block copolymer micelle composition comprising poorly water-soluble drug, an amphiphilic block copolymer containing a hydrophilic block and a hydrophobic block, and an ionizable salt.

Advantageous Effects

The stabilized poorly water-soluble drug-containing amphiphilic block copolymer micelle composition prepared by the method for stabilization according to one embodiment disclosed herein has excellent stability so that it can prevent rapid release of a drug.

BRIEF DESCRIPTION OF THE DRAWINGS

Description will now be given in detail with reference to certain example embodiments of a stabilized poorly water-soluble drug-containing amphiphilic block copolymer micelle composition and a method for stabilizing the same illustrated in the accompanying drawings which are given hereinbelow by way of illustration only and thus are not limitative, wherein.

MODE FOR INVENTION

Figure 1:
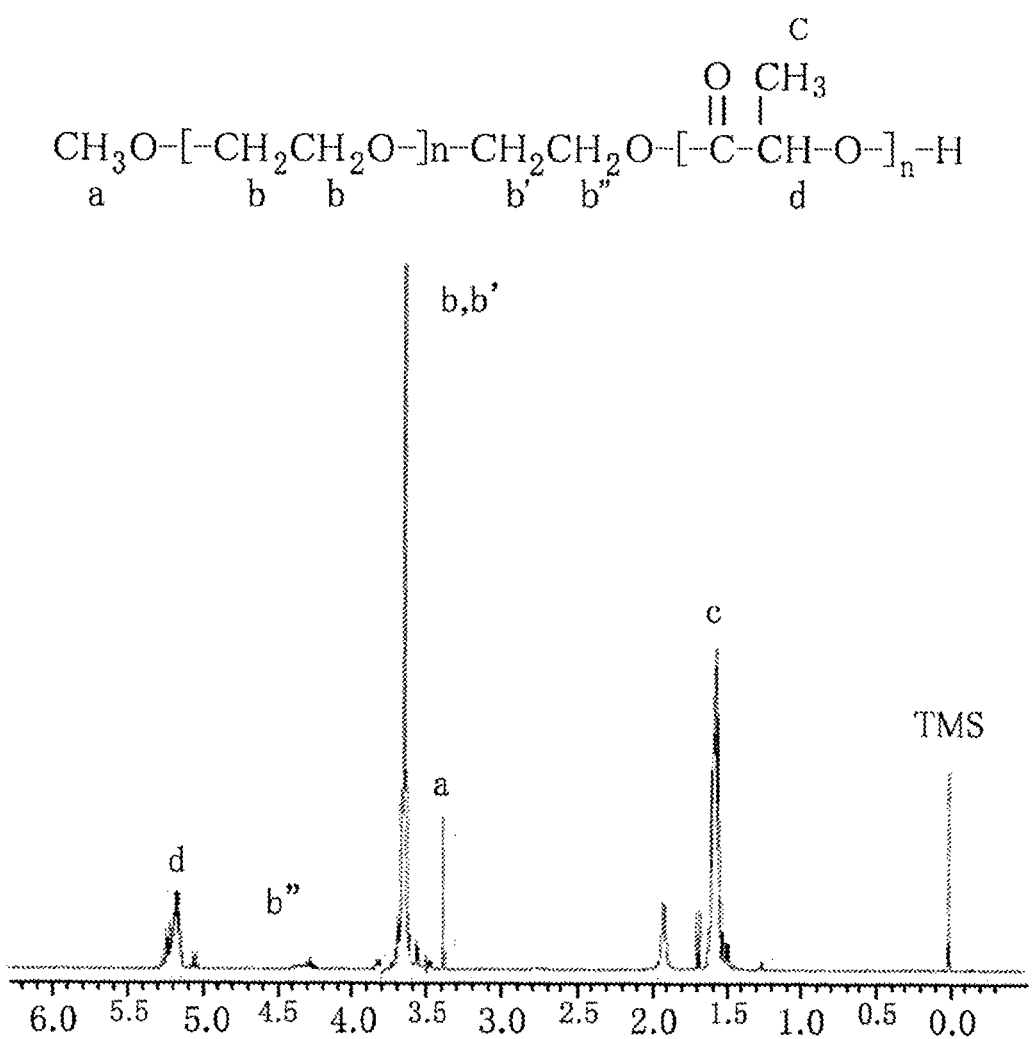
FIG. 1 is the $^1$H NMR spectrum of the diblock copolymer [mPEG-PLA] obtained from Preparation Example 1.

Hereinafter, reference will now be made in detail to various embodiments, examples of which are illustrated in the accompanying drawings and described below. While the invention will be described in conjunction with example embodiments, it will be understood that the present description is not intended to be limitative.

The method for stabilizing a poorly water-soluble drug-containing amphiphilic block copolymer micelle composition according to one embodiment disclosed herein may comprise dissolving poorly water-soluble drug and an amphiphilic block copolymer into an organic solvent to provide a polymer solution; and adding an aqueous solution containing an ionizable salt to the polymer solution to form polymeric micelles, wherein the poorly water-soluble drug-containing amphiphilic block copolymer micelle composition comprises 0.1-30 wt % of poorly water-soluble drug, 20-98 wt % of the amphiphilic block copolymer containing a hydrophilic block (A) and a hydrophobic block (B), and 0.1-50 wt % of the ionizable salt, based on the total dry weight of the composition. The poorly water-soluble drug-containing amphiphilic block copolymer micelle composition has excellent biodegradability and biocompatibility, and provides a polymeric micelle structure having relatively improved stability.

The poorly water-soluble drug may be in an anhydrous or hydrated state, or amorphous or crystalline state. In one embodiment, the poorly water-soluble drug may be present in the composition in an amount of 0.1-30 wt %, specifically 0.5-15 wt %, and more specifically 1-7 wt % based on the total dry weight of the composition.

The term "poorly water-soluble drug" refers to any drug or bioactive agent which has the water solubility of 33.3 mg/ml or less. This includes anticancer agents, antibiotics, anti-inflammatory agents, anesthetics, hormones, antihypertensive agents, and agents for the treatment of diabetes, antihyperlipidemic agents, antiviral agents, agents for the treatment of Parkinson's disease, antidementia agents, antiemetics, immunosuppressants, antiulcerative agents, laxatives, antifungals and antimalarial agents. Examples of poorly water-soluble drugs include taxane, ketoconazole, itraconazole, voriconazole, posaconazole, cyclosporine, cisapride, acetaminophen, aspirin, acetyl salicylic acid, indomethacin, naproxen, wafarin, papaverine, thiabendazole, miconazole, cinarizine, doxorubicin, omeprazole, cholecalciferol, melphalan, nifedipine, digoxin, benzoic acid tryptophan, tyrosine, phenyl alanine, azthreonam, ibuprofen, phenoxymethylpenicillin, thalidomide, methyl testosterone, prochlorperazine, hydrocortisone, dideoxypurine nucleoside, vitamin D2, sulfonamide, sulfonylurea, para-aminobenzoic acid, melatonin, benzyl penicillin, chlorambucil, diazepine, digitoxin, hydrocortisone butyrate, metronidazole benzoate, tobutamide, prostaglandin, fludrocortisone, griseofulvin, miconazole nitrate, leukotriene B4 inhibitor, propranolol, theophylline, flubiprofen, sodium benzoate, benzoic acid, riboflavin, benzodiazepine, phenobarbital, glyburide, sulfadiazine, sulfaethyl thiadiazole, diclofenac sodium, phenyroin, hioridazine hydrochloride, bropyrimie, hydrochlorothiazide, fluconazole, rapamycin and derivatives or analogs thereof such as benzoyl rapamycin, everolimus, temsirolimus, pimecrolimus, biolimus, epothilone A, -B, -D, ixabepilone etc. and pharmaceutically acceptable salts thereof.

In one embodiment, the poorly water-soluble drug is a taxane. Examples of taxane include paclitaxel, docetaxel, 7-epipaclitaxel, t-acetyl paclitaxel, 10-desacetyl-paclitaxel, 10-desacetyl-7-epipaclitaxel, 7-xylosylpaclitaxel, 10-desacetyl-7-glutarylpaclitaxel, 7-N,N-dimethylglycylpaclitaxel, 7-L-alanylpaclitaxel, cabazitaxel or a mixture thereof. Particularly, paclitaxel or docetaxel may be used. A taxane may be extracted from natural plants, or may be obtained by semi-synthesis or plant cell cultivation.

In one embodiment, the amphiphilic block copolymer may comprise a hydrophilic block (A) and a hydrophobic block (B) linked with each other in the form of A-B, A-B-A or B-A-B structure. Additionally, the amphiphilic block copolymer may form core-shell type polymeric micelles in its aqueous solution state, wherein the hydrophobic block forms the core and the hydrophilic block forms the shell.

In one embodiment, the hydrophilic block (A) of the amphiphilic block copolymer may be polyethylene glycol (PEG) or monomethoxypolyethylene glycol (mPEG). Particularly, it may be mPEG. The hydrophilic block (A) may have a weight average molecular weight of 500-20,000 daltons, specifically 1,000-5,000 daltons, and more specifically 1,000-2,500 daltons.

The hydrophobic block (B) of the amphiphilic block copolymer may be a water-insoluble, biodegradable polymer. In one embodiment, the hydrophobic block (B) may be polylactic acid (PLA) or poly(lactic-co-glycolic acid) (PLGA). In another embodiment, the hydrophobic block (B) may have a weight average molecular weight of 500-20,000 daltons, specifically 1,000-5,000 daltons, and more specifically 1,000-2,500 daltons. Hydroxyl end groups of the hydrophobic block (B) may be protected with fatty acid groups, and particular examples of the fatty acid groups include acetate, propionate, butyrate, stearate, palmitate groups, and the like. The amphiphilic block copolymer comprising the hydrophilic block (A) and the hydrophobic block (B) may be present in the composition in an amount of 20-98 wt %, specifically 65-98 wt %, and more specifically 80-98 wt % based on the total dry weight of the composition.

In another embodiment, the hydrophilic block (A) and the hydrophobic block (B) may be present in the amphiphilic block copolymer in such a ratio that the copolymer comprises 40-70 wt %, specifically 50-60 wt % of the hydrophilic block (A) based on the weight of the copolymer. When the hydrophilic block (A) is present in a proportion less than 40%, the polymer has undesirably low solubility to water, resulting in difficulty in forming micelles. On the other hand, when the hydrophilic block (A) is present in a proportion greater than 70%, the polymer becomes too hydrophilic to form stable polymeric micelles, and thus the composition may not be used as a composition for solubilizing poorly water-soluble drug.

The ionizable salt functions to improve the stability of the poorly water-soluble drug-containing amphiphilic block copolymer micelle composition. Particularly, the ionizable salt significantly improves the stability of the composition in its aqueous solution state. One possible mechanism of the function of the ionizable salt is as follows.

The degree of encapsulation of a drug within a polymeric micelle structure is in proportion to the fraction of cores formed from the hydrophobic block of the polymer in an aqueous solution. Additionally, the stability of the polymeric micelles depends on the dynamic equilibrium state formed by the polymeric micelles in an aqueous solution, i.e., on the equilibrium constant between the polymeric micelle state and the unimer state dissolved in water.

Although a large amount of poorly soluble drug can be encapsulated within a polymeric micelle structure, the hydrophilic blocks of the polymer micelles may be surrounded with a great amount of water molecules upon the encapsulation of the drug, and thus the interaction between the water molecules and the hydrophilic blocks may weaken the hydrophobic interaction between hydrophobic blocks of the micelles, thereby destabilizing the micelles in a dynamic equilibrium state. Addition of the ionizable salt causes an electrostatic attraction force between the ionizable salt and water, resulting in dissociation of water molecules from the hydrophilic blocks of the polymeric micelles. As a result, the hydrophobic interaction between the hydrophobic blocks, which otherwise would participate in loose interaction, increases relatively, so that stable micelle structures can be formed. In addition, the ionizable salt is not removed during the preparation of the composition according to one embodiment disclosed herein but remains in the finished composition. Through the stabilization effect realized by the ionizable salt, the poorly water-soluble drug-containing amphiphilic block copolymer micelle composition has excellent stability.

The ionizable salt is pharmaceutically acceptable one and may be selected from any ionizable salts as long as it does not cause hemolysis upon the contact with blood.

In one embodiment, the ionizable salt may be an electrolyte, specifically an inorganic salt. Preferably, the inorganic salt may be at least one selected from the group consisting of sodium chloride, sodium sulfate, magnesium chloride, phosphate salts (e.g. $NaH_2PO_4$, $KH_2PO_4$, $Na_2HPO_4$, $K_2HPO_4$), carbonate salts and bicarbonate salts (e.g. $NaHCO_3$, $Na_2CO_3$, $KHCO_3$, $K_2CO_3$). More particularly, the ionizable salt may be sodium chloride.

In one embodiment, the ionizable salt may be an organic salt. Preferably, the organic salt may be at least one selected from the group consisting of lactate, citrate, malate, succinate, tartarate, fumarate, ascorbate, glutamate, gluconate, sebacinate, malonate, salicylate, acetate and sorbate salts of alkaline metal. More specifically, the organic salt may be at least one selected from the group consisting of sodium lactate, sodium citrate, sodium malate, sodium succinate, sodium tartarate, sodium fumarate, sodium ascorbate, sodium glutamate, sodium gluconate, sodium sebacinate, sodium malonate, sodium salicylate, sodium acetate and potassium sorbate.

Especially, it may be sodium chloride. In another embodiment, the ionizable salt may be present in the composition in an amount of 0.1-50 wt %, specifically 0.5-20 wt %, and more specifically 1-10 wt %, based on the total dry weight of the composition.

In another aspect, there is provided a method for stabilizing a lyophilized composition comprising the poorly water-soluble drug-containing amphiphilic block copolymer micelle composition.

The lyophilized composition may further comprise a lyophilization aid. In one embodiment, the lyophilization aid may be at least one selected from the group consisting of lactose, mannitol, sorbitol and sucrose. The lyophilization aid is added for the lyophilized composition to maintain a cake form. In addition, the lyophilization aid serves to help the amphiphilic block copolymer micelle composition to form homogeneously in short time during the reconstitution of the lyophilized composition. In another embodiment, the lyophilization aid may be used in an amount of 1-90 wt %, and more particularly 10-60 wt %, based on the total dry weight of the lyophilized composition.

In one embodiment, the lyophilized composition may comprise 0.1-15 wt % of poorly water-soluble drug based on the total dry weight of the composition, upon the reconstitution in an aqueous solution. Additionally, upon the reconstitution, the amphiphilic block copolymer may be present at a concentration of 10-150 mg/mL, the ionizable salt may be present at a concentration of 5-30 mg/mL (specifically, 10-20 mg/mL), and the lyophilization aid may be present at a concentration of 1-100 mg/mL. In another embodiment, the lyophilized composition can have a controlled micelle particle size in a range of 1-400 nm, and more particularly 5-200 nm in an aqueous solution, depending on the molecular weight of the copolymer.

In one embodiment, the poorly water-soluble drug-containing amphiphilic block copolymer micelle composition may be formulated into the form of an aqueous solution, powder or tablet. In another embodiment, the composition may be an injection formulation. For example, the composition may be reconstituted with distilled water for injection, 0.9% physiological saline, 5% aqueous dextrose solution, and the like. When the composition is reconstituted, at least 95% of poorly water-soluble drug is stable for 12 hours or more without precipitation.

In another embodiment, the method may further comprise, after step (b):

(c) adding a lyophilization aid to the polymeric micelles; and (d) carrying out lyophilization.

When poorly water-soluble drug is encapsulated with a micelle composition by using an organic solvent via a solvent evaporation process, rapid drug precipitation may occur in the poorly water-soluble drug-containing micelle composition after the composition is reconstituted in injection water and is left at room temperature. This is because the organic solvent used in the solvent evaporation process remains in the composition.

Therefore, according to one embodiment of the method disclosed herein, drug precipitation may be prevented by using an ionizable salt and a minimized amount of organic solvent. To minimize the amount of the organic solvent still remaining in the finished composition, the composition needs to be dried at a high temperature of 60° C. or higher under reduced pressure for at least 12 hours. However, such reduced-pressure, high-temperature drying conditions may cause degradation of a drug. Thus, the method for stabilizing the poorly water-soluble drug-containing amphiphilic block copolymer micelle composition according to one embodiment disclosed herein uses a minimized amount of organic solvent so that the finished composition can be directly subjected to lyophilization while avoiding a need for a separate step of removing the organic solvent. [0041] The poorly water-soluble drug-containing amphiphilic block copolymer micelle composition containing the ionizable salt and using a minimized amount of organic solvent according to one embodiment disclosed herein can provide a lyophilized composition which is free from precipitation of poorly water-soluble drug for 12 hours or more when reconstituted into an injection formulation.

In one embodiment, the organic solvent in step (a) may include at least one selected from the group consisting of acetone, ethanol, methanol, ethyl acetate, acetonitrile, methylene chloride, chloroform, acetic acid and dioxane. The organic solvent may be used in an amount of 0.5-30 wt %, specifically 0.5-15 wt %, and more specifically 1-10 wt % based on the weight of the resultant micelle composition. When the organic solvent is used in an amount less than 0.5 wt %, there may be a difficulty in dissolving a drug. On the other hand, when the organic solvent is used in an amount greater than 30 wt %, drug precipitation may occur upon the reconstitution of the lyophilized composition.

In one example embodiment, the ionizable salt may be at least one selected from the group consisting of sodium chloride, sodium sulfate and magnesium chloride. In addition, the ionizable salt may be used in an amount of 0.1-50 wt % based on the total dry weight of the micelle composition. Step (b) may be performed at a temperature of 25° C. or lower.

In one embodiment, the method for stabilizing the poorly water-soluble drug-containing amphiphilic block copolymer micelle composition may further comprise sterilizing the aqueous polymeric micelle solution obtained from step (c) with a sterilization filter, before step (d) of carrying out lyophilization.

The poorly water-soluble drug-containing amphiphilic block copolymer micelle composition according to one embodiment disclosed herein may be orally or parenterally administered in the form of an aqueous solution or powder. Parenteral administration includes administration via intravascular, intramuscular, subcutaneous, intraperitoneal, nasal, rectal, ophthalmic, pulmonary or other routes. Oral administration includes administration in the form of tablets or capsules, or aqueous solution itself.

In addition, the lyophilized composition according to one embodiment disclosed herein causes little variation in the concentration of docetaxel in a reconstituted composition over time. However, when no ionizable salt is added, docetaxel concentration decreases after the lapse of one hour.

The following examples are not intended to be limitative.

PREPARATION EXAMPLE 1

Synthesis of Monomethoxypolyethylene Glycol-Polylactide (mPEG-PLA) Block Copolymer (A-B Type)

First, 5.0 g of monomethoxypolyethylene glycol (number average molecular weight: 2,000 daltons) is introduced into a 100 mL two-neck round-bottom flask, and is heated to 130° C. under reduced pressure (1 mmHg) for 3-4 hours to remove water therefrom. Next, the flask is purged with nitrogen gas, and stannous octoate (Sn(Oct)$_2$) is added thereto as a reaction catalyst using a syringe in an amount of 0.1 wt % (10.13 mg, 25 mmol) based on the weight of D- and L-lactides. After the reaction mixture is agitated for 30 minutes, it is subjected to depressurization (1 mmHg) at 130° C. for 1 hour to remove the solvent (toluene) in which the catalyst is dissolved. Then, 10.13 g of purified lactide is added thereto, and the resultant mixture is heated at 130° C. for 18 hours. After heating, the resultant polymer is dissolved into methylene chloride, and is added to diethyl ether to cause precipitation of the polymer. The resultant polymer is dried in a vacuum oven for 48 hours.

The copolymer, monomethoxylpolyethylene glycol-polylactide (mPEG-PLA), has a number average molecular weight of 2,000-1,765 daltons. Analysis of the copolymer performed by $^1$H-NMR reveals that the copolymer is an A-B type diblock copolymer (see FIG. 1).

PREPARATION EXAMPLE 2

Synthesis of Monomethoxypolyethylene Glycol-Poly(Lactic-Co-Glycolic Acid) (mPEG-PLGA) Block Copolymer (A-B Type)

A block copolymer is obtained by reacting monomethoxypolyethylene glycol (number average molecular weight: 5,000 daltons), lactide and glycolide in the presence of stannous octoate as a catalyst at 120° C. for 12 hours in the same manner as Preparation Example 1.

Figure 2:
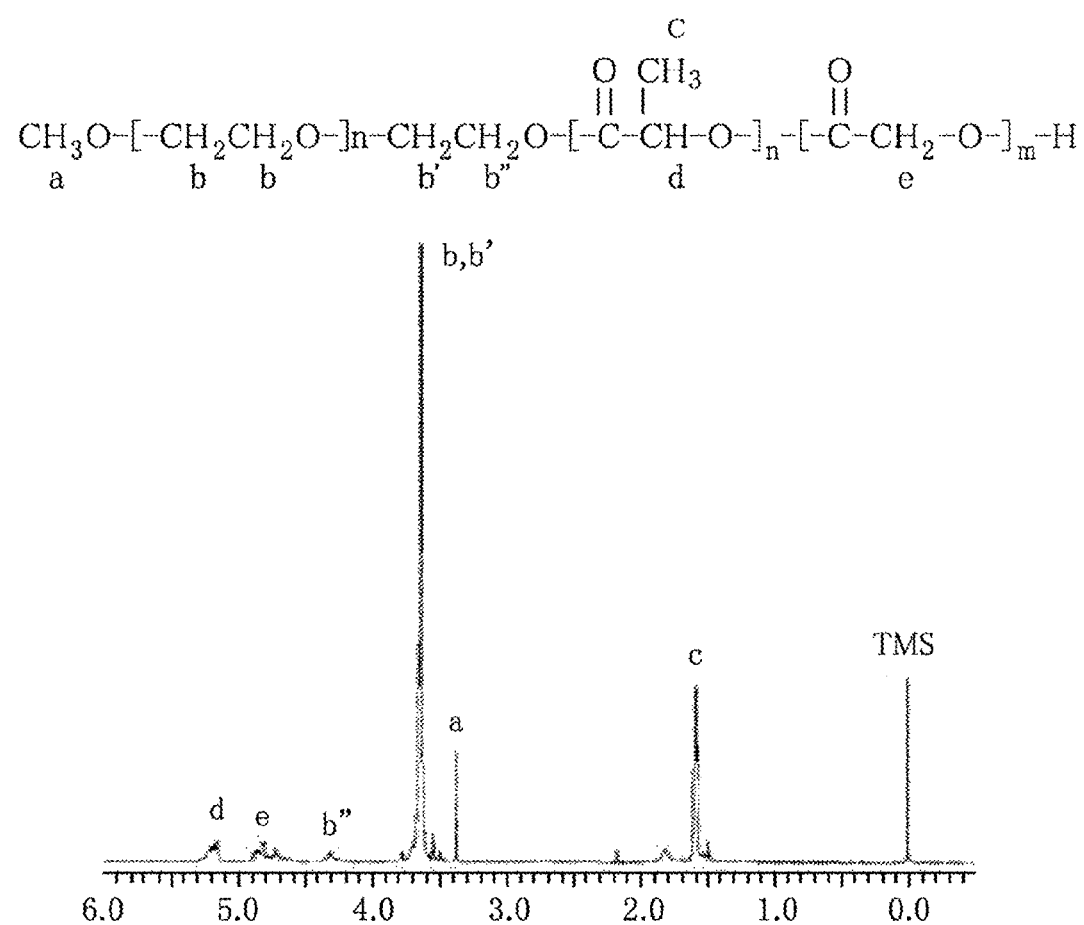
FIG. 2 is the $^1$H NMR spectrum of the diblock copolymer [mPEG-PLGA] obtained from Preparation Example 2.

The copolymer, monomethoxypolyethylene glycol-poly(lactic-co-glycolic acid) (mPEG-PLGA), has a number average molecular weight of 5,000-4,000 daltons and is an A-B type copolymer. Analysis of the copolymer performed by $^1$H-NMR reveals that the copolymer is an A-B type diblock copolymer (see FIG. 2).

EXAMPLE 1

Preparation of Mpeg-PLA Block Copolymer Micelle Composition Containing Sodium Chloride and Docetaxel First, 760 mg of the amphiphilic block copolymer, mPEG-PLA (number average molecular weight: 2,000-1,765 daltons), obtained from Preparation Example 1 is completely dissolved into 0.2 mL of ethanol at 60° C. to provide a clear ethanol solution comprising the copolymer. The ethanol solution is cooled to 25° C., and 20 mg of docetaxel is added thereto and the resultant solution is agitated until docetaxel is completely dissolved.

Next, aqueous solutions each containing 0.9 wt % and 1.8 wt % of sodium chloride are prepared in separate containers. Each aqueous solution is added to the ethanol solution comprising the copolymer in an amount of 4 mL, and the resultant mixture is agitated at 40° C. for 10 minutes to form an aqueous polymeric micelle solution.

Then, 100 mg of D-mannitol is dissolved into each solution, and the resultant solution is filtered through a filter with a pore size of 200 nm to remove undissolved docetaxel, followed by lyophilization.

The lyophilized composition is subjected to liquid chromatography as follows to determine the content of docetaxel. Additionally, particle size is measured by a dynamic light scattering (DLS) method. The results are shown in the following Table 1

TABLE 1

| (mg) | (mg) | | Docetaxel Content (wt %) | Particle Size (nm) |
|---|---|---|---|---|
| 760 | 20 | 36 | 99.9 | 18 |
| 760 | 20 | 72 | 99.8 | 19 |

Liquid Chromatography
  1) Column: a stainless steel column having a length of 250 mm and an inner diameter of 4.6 mm and packed with pentafluorophenyl-coated particles having a particle diameter of 5 μm and a pore diameter of 300 Å.
  2) Mobile Phase: acetonitrile:methanol:water=26:32:420
  3) Flow Rate: 1.5 mL/min
  4) Loading Amount: 20 μL
  5) Detector: UV absorption spectrometer (measurement wavelength: 232 nm)

EXAMPLE 2

Preparation of Mpeg-PLA Block Copolymer Micelle Composition Containing Magnesium Chloride and Paclitaxel First, 100 mg of the amphiphilic block copolymer, mPEG-PLA (number average molecular weight: 2,000-1,765 daltons), obtained from Preparation Example 1 is completely dissolved into 0.1 mL of ethanol at 60° C. to provide a clear ethanol solution comprising the copolymer. The ethanol solution is cooled to 25° C., and 20 mg of paclitaxel is added thereto and the resultant solution is agitated until paclitaxel is completely dissolved.

Next, aqueous solutions each containing 0.9 wt % and 1.8 wt % of -magnesium chloride are prepared in separate containers. Each aqueous solution is added to the ethanol solution comprising the copolymer in an amount of 4 mL, and the resultant mixture is agitated at 40° C. for 10 minutes to form an aqueous polymeric micelle solution.

Then, 39 mg of D-mannitol is dissolved into each solution, and the resultant solution is filtered through a filter with a pore size of 200 nm to remove undissolved paclitaxel, followed by lyophilization.

The lyophilized composition is subjected to the liquid chromatography as described in Example 1 to determine the content of paclitaxel. Additionally, particle size is measured by a DLS method. The results are shown in the following Table 2.

TABLE 2

| mPEG-PLA (mg) | Paclitaxel (mg) | MgCl$_2$ (mg) | Paclitaxel Content (wt %) | Particle Size (nm) |
|---|---|---|---|---|
| 100 | 20 | 36 | 99.7 | 21 |
| 100 | 20 | 72 | 99.9 | 22 |

EXAMPLE 3

Preparation of Mpeg-PLGA Block Copolymer Micelle Composition Containing Sodium Chloride and Docetaxel First, 760 mg of the amphiphilic block copolymer, mPEG-PLGA (number average molecular weight: 5,000-4,000 daltons), obtained from Preparation Example 2 is completely dissolved into 0.2 mL of acetone at 50° C. to provide a clear acetone solution comprising the copolymer. The acetone solution is cooled to 25° C., and 40 mg of docetaxel is added thereto and the resultant solution is agitated until docetaxel is completely dissolved.

Next, 8 mL of an aqueous solution containing 0.9 wt % of sodium chloride is added to the acetone solution comprising the copolymer and further containing the drug, and the resultant mixture is agitated at 25° C. for 20 minutes to form a homogeneous solution. Once the homogeneous solution is formed, 200 mg of D-mannitol is dissolved into the solution to provide a clear aqueous polymeric micelle solution. Finally, the aqueous polymeric micelle solution is filtered through a filter with a pore size of 200 nm to remove undissolved docetaxel, followed by lyophilization.

The lyophilized composition is subjected to the liquid chromatography as described in Example 1 to determine the content of docetaxel. Additionally, particle size is measured by a DLS method.

Docetaxel content: 101.3 wt %.
Particle size: 35 nm.

EXAMPLE 4

Preparation of Mpeg-PLGA Block Copolymer Micelle Composition Containing Magnesium Chloride and Paclitaxel First, 100 mg of the amphiphilic block copolymer, mPEG-PLGA (number average molecular weight: 5,000-4,000 daltons), obtained from Preparation Example 2 is completely dissolved into 0.2 mL of acetone at 50° C. to provide a clear acetone solution comprising the copolymer. The acetone solution is cooled to 25° C., and 40 mg of paclitaxel is added thereto and the resultant solution is agitated until paclitaxel is completely dissolved.

Next, 8 mL of an aqueous solution containing 0.9 wt % of magnesium chloride is added to the acetone solution comprising the copolymer and further containing the drug, and the resultant mixture is agitated at 25° C. for 20 minutes to form a homogeneous solution. Once the homogeneous solution is formed, 53 mg of D-mannitol is dissolved into the solution to provide a clear aqueous polymeric micelle solution. Finally, the aqueous polymeric micelle solution is filtered through a filter with a pore size of 200 nm to remove undissolved paclitaxel, followed by lyophilization.

The lyophilized composition is subjected to high-performance liquid chromatography (HPLC) to determine the content of docetaxel. Additionally, particle size is measured by a DLS method.

Docetaxel content: 99.7 wt %.
Particle size: 37 nm.

COMPARATIVE EXAMPLE 1

Preparation of Mpeg-PLA Block Copolymer Micelle Composition Containing No Inorganic Salt First, 760 mg of the amphiphilic block copolymer, mPEG-PLA (number average molecular weight: 2,000-1,765 daltons), obtained from Preparation Example 1 is completely dissolved into 0.2 mL of ethanol at 60° C. to provide a clear ethanol solution comprising the copolymer. The ethanol solution is cooled to 25° C., and 20 mg of docetaxel is added thereto and the resultant solution is agitated until docetaxel is completely dissolved.

Next, 4 mL of distilled water for injection is added to the ethanol solution comprising the copolymer, and the resultant mixture is agitated at 40° C. for 10 minutes to form a homogeneous solution. Once the homogeneous solution is formed, 100 mg of D-mannitol is dissolved into the solution to provide a clear aqueous polymeric micelle solution. Finally, the aqueous polymeric micelle solution is filtered through a filter with a pore size of 200 nm to remove undissolved docetaxel, followed by lyophilization.

The lyophilized composition is subjected to HPLC to determine the content of docetaxel. Additionally, particle size is measured by a DLS method.
Docetaxel content: 100.3 wt %.
Particle size: 18 nm.

EXPERIMENTAL EXAMPLE 1

Stability Test

The sodium chloride-containing polymeric micelle compositions according to Example 1 are compared with the polymeric micelle composition containing no inorganic salt according to Comparative Example 1 in terms of the stability of the aqueous solution at 37° C.

Each of the lyophilized compositions according to Example 1 and Comparative Example 1 is diluted with distilled water for injection to a docetaxel concentration of 1 mg/mL. While each diluted solution is left at 37° C., concentration of docetaxel contained in each micelle structure is measured over time. The results are shown in the following Table 3.

TABLE 3

|  | mPEG-PLA (mg) | Docetaxel (mg) | NaCl (mg) | Initial Docetaxel Concentration (mg/mL) | Docetaxel Concentration After 12 Hours (mg/mL) |
|---|---|---|---|---|---|
| Comp. Ex. 1 | 760 | 20 | 0 | 1.0 | 0.41 |
| Ex. 1 | 760 | 20 | 36 | 1.0 | 0.95 |
|  | 760 | 20 | 72 | 1.0 | 0.99 |

As can be seen from the results of Table 3, the compositions according to Example 1 cause no precipitation of docetaxel even after the lapse of 12 hours, while the composition according to Comparative Example 1 shows an amount of docetaxel precipitation of 59% after the lapse of 12 hours. It can be seen from the above results that addition of sodium chloride may increase the docetaxel retainability of a micelle composition by about at least two times. Additionally, it can be also seen that a higher ratio of the amount of the inorganic salt to that of the amphiphilic block copolymer provides the micelle composition with higher stability.

EXAMPLES 5~8 AND COMPARATIVE EXAMPLE 2

Preparation of mPEG-PLA Block Copolymer Micelle Composition Containing Various Ionizable Salts and Docetaxel First, 380 mg of the amphiphilic block copolymer, mPEG-PLA (number average molecular weight: 2,000-1,765 daltons), obtained from Preparation Example 1 is completely dissolved into 2.0 mL of ethanol at 60° C. to provide a clear ethanol solution comprising the copolymer. The ethanol solution is cooled to 30° C., and 20 mg of docetaxel is added thereto and the resultant solution is agitated until docetaxel is completely dissolved. The ethanol is completely evaporated from the solution by using a rotary evaporator to form a polymer-drug matrix.

Next, aqueous solutions each containing ionizable salts are prepared in separate containers. Each aqueous solution is added to the polymer-drug matrix, and the resultant mixture is agitated at 30° C. for 10 minutes to form an aqueous polymeric micelle solution.

Then, 100 mg of D-mannitol is dissolved into each solution, and the resultant solution is filtered through a filter with a pore size of 200 nm to remove undissolved docetaxel, followed by lyophilization.

The lyophilized composition is reconstituted with water for injection (WFI) and subjected to high pressure liquid chromatography to determine the content of docetaxel. Additionally, particle size is measured by a dynamic light scattering (DLS) method. The results are shown in the following Table 4.

TABLE 4

|  | Examples | | | | Comparative Example 2 |
|---|---|---|---|---|---|
| Components | Example 5 | Example 6 | Example 7 | Example 8 |  |
| Docetaxel (mg) | 20.0 | 20.0 | 20.0 | 20.0 | 20.0 |
| mPEG-PLA (mg) | 380.0 | 380.0 | 380.0 | 380.0 | 380.0 |
| Sodium Citrate (mg) | 58.8 | — | — | — | — |
| Sodium Carbonate (mg) | — | 12.4 | — | — | — |
| Sodium Phosphate, monobasic (mg) | — | — | 36.0 | — | — |
| Sodium Acetate (mg) | — | — | — | 16.4 | — |
| D-Mannitol (mg) | 100.0 | 100.0 | 100.0 | 100.0 | 100.0 |
| WFI | 19.5 | 19.5 | 19.5 | 19.5 | 19.5 |
| Particle Size (nm) | 20.2 | 19.9 | 19.9 | 19.0 | 20.9 |
| pH | 7.6 | 9.9 | 4.5 | 6.6 | 4.4 |
| Initial Docetaxel Concentration (mg/mL) | 1.0 | 1.0 | 1.0 | 1.0 | 1.0 |
| Docetaxel Concentration After 24 hr Incubation at 25° C. (mg/mL) | 0.92 | 0.96 | 0.94 | 0.95 | 0.57 |

EXAMPLES 9~12 AND COMPARATIVE EXAMPLE 3

Preparation of mPEG-PLA Block Copolymer Micelle Composition Containing Various Ionizable Salts and Paclitaxel First, 500 mg of the amphiphilic block copolymer, mPEG-PLA (number average molecular weight: 2,000-1,765 daltons), obtained from Preparation Example 1 is completely dissolved into 2.0 mL of ethanol at 60° C. to provide a clear ethanol solution comprising the copolymer. The ethanol solution is cooled to 40° C., and 100 mg of paclitaxel is added thereto and the resultant solution is agitated until paclitaxel is completely dissolved. The ethanol is completely evaporated from the solution by using a rotary evaporator to form a polymer-drug matrix.

Next, aqueous solutions each containing ionizable salts are prepared in separate containers. Each aqueous solution is added to the polymer-drug matrix, and the resultant mixture is agitated at 40° C. for 10 minutes to form an aqueous polymeric micelle solution.

Then, 250 mg of anhydrous lactose is dissolved into each solution, and the resultant solution is filtered through a filter with a pore size of 200 nm to remove undissolved paclitaxel, followed by lyophilization.

The lyophilized composition is reconstituted with water for injection (WFI) and subjected to liquid chromatography to determine the content of paclitaxel. Additionally, particle size is measured by a dynamic light scattering (DLS) method. The results are shown in the following Table 5.

TABLE 5

| Components | Examples | | | | Comparative Example 3 |
| --- | --- | --- | --- | --- | --- |
| | Example 9 | Example 10 | Example 11 | Example 12 | |
| Paclitaxel (mg) | 100.0 | 100.0 | 100.0 | 100.0 | 100.0 |
| mPEG-PLA (mg) | 500.0 | 500.0 | 500.0 | 500.0 | 500.0 |
| Sodium Citrate (mg) | 58.8 | — | — | — | — |
| Sodium Carbonate(mg) | — | 12.4 | — | — | — |

TABLE 5

| Components | Examples | | | | Comparative Example 3 |
| --- | --- | --- | --- | --- | --- |
| | Example 9 | Example 10 | Example 11 | Example 12 | |
| Sodium Phosphate, monobasic (mg) | — | — | 36.0 | — | — |
| Sodium Acetate (mg) | — | — | — | 16.4 | — |
| Anhydrous lactose (mg) | 250.0 | 250.0 | 250.0 | 250.0 | 250.0 |
| WFI | 19.5 | 19.5 | 19.5 | 19.5 | 19.5 |
| Particle Size (nm) | 21.2 | 19.8 | 19.7 | 19.4 | 19.7 |
| pH | 6.8 | 9.6 | 3.4 | 5.5 | 3.1 |
| Initial Paclitaxel Concentration (mg/mL) | 5.0 | 5.0 | 5.0 | 5.0 | 5.0 |
| Paclitaxel Concentration After 24 hr Incubation at 25° C. (mg/mL) | 4.76 | 4.91 | 4.72 | 4.83 | 4.61 |

EXAMPLES 13~14 AND COMPARATIVE EXAMPLE 4

Preparation of mPEG-PLA Block Copolymer Micelle Composition Containing Various Ionizable Salts and Temsirolimus First, 390 mg of the amphiphilic block copolymer, mPEG-PLA (number average molecular weight: 2,000-1,765 daltons), obtained from Preparation Example 1 is completely dissolved into 2.0 mL of dichloromethane at 60° C. to provide a clear dichloromethane solution comprising the copolymer. The dichloromethane solution is cooled to 40° C., and 25 mg of temsirolimus is added thereto and the resultant solution is agitated until temsirolimus is completely dissolved. The dichloromethane is completely evaporated from the solution by using a rotary evaporator to form a polymer-drug matrix.

Next, aqueous solutions each containing ionizable salts are prepared in separate containers. Each aqueous solution is added to the polymer-drug matrix, and the resultant mixture is agitated at 40° C. for 10 minutes to form an aqueous polymeric micelle solution.

Then, 275 mg of D-mannitol is dissolved into each solution, and the resultant solution is filtered through a filter with a pore size of 200 nm to remove undissolved temsirolimus, followed by lyophilization.

The lyophilized composition is reconstituted with water for injection (WFI) and subjected to liquid chromatography to determine the content of temsirolimus. Additionally, particle size is measured by a dynamic light scattering (DLS) method. The results are shown in the following Table 6.

TABLE 6

| Components | Examples | | Comparative Example 4 |
| --- | --- | --- | --- |
| | Example 13 | Example 14 | |
| Temsirolimus (mg) | 25.0 | 25.0 | 25.0 |
| mPEG-PLA(mg) | 287.5 | 287.5 | 287.5 |
| Sodium Chloride (mg) | 90.0 | — | — |
| Sodium Phosphate, monobasic (mg) | — | 36.0 | — |
| D-Mannitol (mg) | 275.0 | 275.0 | 275.0 |
| WFI (mL) | 9.5 | 9.5 | 9.5 |
| Particle Size (nm) | 21.7 | 20.9 | 22.9 |
| pH | 3.2 | 3.4 | 3.1 |
| Initial Temsirolimus Concentration (mg/mL) | 2.50 | 2.50 | 2.50 |
| Temsirolimus Concentration After 24 hr Incubation at 25° C. (mg/mL) | 2.46 | 2.48 | 2.23 |

Description has been given in detail with reference to example embodiments. However, it will be appreciated by those skilled in the art that changes may be made in these embodiments without departing from the principles and spirit of the method for stabilizing the poorly water-soluble drug-containing amphiphilic block copolymer micelle composition, the scope of which is defined in the accompanying claims and their equivalents.

We claim:

1. A taxane-containing amphiphilic block copolymer micelle formation aqueous solution, consisting of 1.0-15 wt % of paclitaxel or docetaxel, 20-98wt % of an amphiphilic block copolymer containing a hydrophilic block (A) and a hydrophobic block (B), and 1.0-10 wt % of sodium chloride, in an aqueous ethanol solution, wherein the weight percentages are based on the total dry weight of the taxane-containing amphiphilic block copolymer micelle aqueous solution,
wherein the hydrophilic block (A) is polyethylene glycol or monomethoxypolyethylene glycol having a weight average molecular weight of 1,000-2,500 daltons, and the hydrophobic block (B) is polylactic acid (PLA) or a copolymer of polylactic acid and glycolic acid (PLGA) having a weight average molecular weight of 1,000-2,500 daltons, and
wherein the amphiphilic block copolymer comprises 50-60 wt % of the hydrophilic block (A) and 40-50 wt % of the hydrophobic block (B).

2. A reconstituted taxane-containing amphiphilic block copolymer micelle aqueous solution for intravenous infusion, consisting of 0.1-15 wt % of paclitaxel or docetaxel, based on the total dry weight of the aqueous solution, 10-150 mg/ml of an amphiphilic block copolymer containing a hydrophilic block (A) and a hydrophobic block (B), 5-30 mg/ml of sodium chloride, and 1-100 mg/ml of lactose or mannitol, wherein the hydrophilic block (A) is polyethylene glycol or monomethoxypolyethylene glycol having a weight average molecular weight of 1,000-2,500 daltons, and the hydrophobic block (B) is polylactic acid (PLA) or a copolymer of polylactic acid and glycolic acid (PLGA) having a weight average molecular weight of 1,000-2,500 daltons, and wherein the amphiphilic block copolymer comprises 50-60 wt % of the hydrophilic block (A) and 40-50 wt % of the hydrophobic block (B).

* * * * *